United States Patent [19]

Turner et al.

[11] Patent Number: 5,073,372

[45] Date of Patent: * Dec. 17, 1991

[54] LEAVE-ON FACIAL EMULSION COMPOSITIONS

[75] Inventors: Deborah J. Turner, Naugatuck; Arvind M. Mehta, Woodbridge; Jeanne M. Foley, West Haven; Darrell G. Doughty, Shelton, all of Conn.

[73] Assignee: Richardson-Vicks, Inc., Shelton, Conn.

[ * ] Notice: The portion of the term of this patent subsequent to Dec. 17, 2008 has been disclaimed.

[21] Appl. No.: 621,167

[22] Filed: Nov. 30, 1990

[51] Int. Cl.$^5$ ............................ A61K 7/00; A61K 31/78
[52] U.S. Cl. ....................................... 424/401; 424/59; 424/60; 424/617; 514/937; 514/772.6
[58] Field of Search ....................................... 424/401, 81

[56] References Cited

U.S. PATENT DOCUMENTS

| Re. 29,814 | 10/1978 | Snyder | 424/81 |
|---|---|---|---|
| 4,515,784 | 5/1985 | Bogardus et al. | 514/63 |
| 4,529,588 | 7/1985 | Smith et al. | 424/70 |
| 4,593,021 | 6/1986 | Hsia et al. | 424/401 |
| 4,728,457 | 3/1988 | Fieler et al. | 252/174.15 |
| 4,741,855 | 5/1988 | Grote et al. | 252/142 |
| 4,837,019 | 6/1989 | Georgalas et al. | 424/81 |
| 4,859,456 | 8/1989 | Marschner | 424/47 |
| 4,973,473 | 11/1990 | Schneider et al. | 424/63 |
| 4,978,526 | 12/1990 | Gesslein et al. | 424/70 |

FOREIGN PATENT DOCUMENTS 0327379  8/1989  European Pat. Off.

OTHER PUBLICATIONS

Gennaro, (1985), Remington's Pharmaceutical Sciences, Mack Publishing Co., 17th Ed.

Primary Examiner—Thurman K. Page
Assistant Examiner—Raj Bawa
Attorney, Agent, or Firm—Anthony D. Sabatelli; David K. Dabbiere; Douglas C. Mohl

[57] ABSTRACT

Disclosed are leave-on facial emulsion compositions that are substantially free from fats and oils and anionic surfactants, which provide improved control of sebum distribution over the surface of the skin. These compositions provide improved cosmetic benefits in terms of the control of the undesirable appearance and tactile sensation of oily skin.

20 Claims, No Drawings

LEAVE-ON FACIAL EMULSION COMPOSITIONS

TECHNICAL FIELD

The present invention relates to leave-on facial emulsion compositions containing cationic surfactants and non-volatile organopolysiloxanes, and which are also substantially free from fats and oils and anionic surfactants, useful for improving the appearance of the skin by controlling the distribution of sebum upon the skin surface.

BACKGROUND OF THE INVENTION

Sebum, or skin oil, is produced in the sebaceous glands located in the pilosebaceous apparatus of the skin and reaches the skin surface through the duct of the hair follicles. The presence of excessive amounts of sebum on the skin surface often results in an unattractive cosmetic condition commonly known as "oily skin". Sebum also plays an important role in the pathogenesis of acne. Sebaceous gland activity is significantly increased in acne subjects, and individuals with the most severe acne often have the highest sebum secretion rates.

The spreading of sebum on the skin surface is thus an important cosmetic parameter since its distribution on the skin surface can determine the appearance of oiliness or greasiness and can contribute to the severity of acne.

It is advantageous, therefore, to have available means for controlling the distribution of sebum over the surface of human skin, with particular regard to skin characterized by an excessive secretion or presence of sebum upon the surface and to affected skin areas of, for example, acne patients.

Currently marketed leave-on facial emulsion products do not effectively control the distribution of sebum upon the surface of the skin. Without being limited by theory, it is believed that current leave-on emulsion products undesirably modify the surface properties of the skin, thereby increasing the contact angle of the sebum with the skin and thus preventing its spreading. These products cause the secreted sebum to remain as small discreet droplets upon the skin, thus resulting in oily skin and its attendant problems.

Typically, the problem of oily facial skin has been dealt with by frequent cleansing and the use of astringent preparations. However, such remedies are of questionable efficacy and not always practical, and also have the disadvantage of drying, irritating, and abrading the skin. Additionally, any benefits which may be obtained through cleansing and the use of astringents are only temporary. Once the skin has been cleansed of sebum, the skin begins secreting sebum anew so that the oily skin problem soon returns.

The prior art teaches the incorporation of clays, talcs, silicas, starches, polymers, and other such materials into skin care products for absorbing sebum and controlling oily skin. See U.S. Pat. No. 4,940,578, Yoshihara, T. et al., issued July 10, 1990; U.S. Patent 4,885,109, to Umemoto, I. et al., issued Dec. 5, 1989; U.S. Pat. No. 4,536,399, to Flynn, R. G. et al., issued Aug. 20, 1985; U.S. Pat. No. 4,489,058, to Lay, G. E. et al., issued Dec. 18, 1984; U.S. Pat. No. 4,388,301, to Klein, R. W., issued June 14, 1983; and U.S. Pat. No. 4,000,317, to Menda W. C. et al., issued Dec. 28, 1976. However, the practicality of incorporating sebum absorbing materials is limited by the sebum absorbing capacity of the material, formulation difficulties, and the negative aesthetic properties which these materials impart to finished products. Also, any oil control benefit which may be obtained is merely temporary.

A longer lasting method of reducing sebum on the skin is through the use of topical or systemic agents believed to provide a sebosuppressive effect. See Karg, G. et al., "Sebosuppression", Cosmetics & Toiletries. vol. 102, pp. 140-146 (April 1987); U.S. Pat. No. 4,593,021, to Hsia, S. L. et al., issued June 3, 1986; U.S. Pat. No. 4,587,235, to Bittler, D. et al., issued May 6, 1986; U.S. Pat. No. 4,529,587, to Green, M. R., issued July 16, 1985; ; U.S. Pat. No. 4,210,654 to Bauer et al., issued July 1, 1980; and U.S. Pat. No. 4,016,287, to Eberhardt et al., issued Apr. 5, 1977. Without being limited by theory, it is believed that sebosuppressive agents decrease the sebum output of the pilosebaceous ducts of the skin, thereby reducing surface oiliness. However, many sebosuppressive agents are potent drugs having undesirable side effects on diuretic activity, inflammation mediators, blood pressure, hormonal levels, cholesterol synthesis, and other bodily functions. Thus, it may not always be practical, desirable, or even possible to utilize sebosuppressive agents to control oily skin.

The control of sebum spreading via topical formulations which do not contain sebosuppressive agents is described in Australian Patent Application 8,319,558 to Herstein et al., published Apr. 12, 1984. This patent discloses formulations for use on oily skin such as cleansers, shampoos, and anti-acne treatments, which contain y-gluconamidopropyl dimethyl 2-hydroxyethyl ammonium chloride. However, these formulations have the undesirable characteristic of increasing the contact angle of sebum with the skin and inhibiting the even spreading and distribution of the sebum. Also, none of the formulations disclosed are leave-on emulsion type lotions or creams.

Furthermore, in addition to the limitations of the prior art discussed above, most currently marketed emulsion products actually contribute to and aggravate oily skin problems. Most emulsion products are oil-in-water or water-in-oil emulsions containing high levels of fats and oils. The high levels of fats and oils in these products give them their characteristic heavy and greasy aesthetics and contribute to oily skin problems. The limited number of products which claim to be free from fats and oils are usually not emulsion type products, but instead are low viscosity, hydro-alcoholic formulations which are too harsh and astringent for regular or frequent use.

Other cosmetic compositions are disclosed in, for example U.S. Pat. No. 4,387,019 to Georgalas et al., issued June 16, 1989 and also in U.S. Pat. No. 4,863,725 to Deckner et al., issued Sept. 5, 1989, both of which are incorporated by reference herein.

Therefore, it would be highly desirable to develop leave-on facial emulsion compositions which overcome the disadvantages of the prior art.

It is therefore an object of the present invention to provide leave-on facial emulsion compositions which reduce the oily appearance and greasy feel of facial skin. It is another object of the present invention to provide compositions for controlling the distribution of sebum upon the skin surface. It is still another object of the present invention to provide compositions which are aesthetically pleasing and substantially free from fats and oils. It is yet another object of the present invention to provide compositions for controlling sebum distribution without incorporating oil-absorbing materials. It is a further object of the present invention to provide compositions for controlling sebum distribution without using sebosuppressive drug agents. It is an even further object of the present invention to provide compositions which reduce the contact angle between sebum and skin. It is yet a further object of the present invention to provide compositions which distribute sebum evenly across the surface of the skin. It is another object of the present invention to retard the regreasing of the skin by sebum. It is yet another object of the present invention to provide methods for reducing the oily appearance and greasy feel of facial skin.

These and other objects of this invention will become apparent in light of the following disclosure.

SUMMARY OF THE INVENTION

The present invention relates to a leave-on facial emulsion composition, substantially free from fats and oils and anionic surfactnats, comprising: (a) from about 0.01 to about 5% of a cationic surfactant; (b) from about 0.1 to about 10% of a non-volatile organopolysiloxane having an average molecular weight of at least 200,000; (c) from about 0.01 to about 5% of one or more of a carboxylic acid copolymer; (d) from about 1% to about 10% of a humectant; and (e) a cosmetically acceptable carrier; wherein said composition provides a contact angle between sebum and skin from 0° to about 10°, and a spreading index for sebum migration greater than about 8500 pixels over the time period from 0-5 minutes.

The present invention further relates to methods for controlling the distribution of sebum on facial skin.

Ingredients are identified by chemical or CTFA name.

All percentages and ratios used herein are by weight unless otherwise indicated.

All measurements are at 25° C. unless otherwise indicated.

DETAILED DESCRIPTION OF THE INVENTION

The term "leave-on", as used herein to modify the term "facial emulsion composition", is used to indicate that the compositions of the present invention are intended to be applied to and allowed to remain on the skin. These leave on compositions are to be distinguished from compositions which are applied to the skin and subsequently removed either by washing, rinsing, wiping, or the like.

The term "substantially free from fats and oils" is defined as meaning that the compositions of the present invention do not contain ingredients that are typically considered by those skilled in the art to constitute a fat and/or oil ingredient. Strictly speaking, fats are defined as naturally occurring esters of long chain carboxylic acids and glycerin, i.e. glyceryl fatty acid esters. Fats which are liquids at room temperature are commonly defined as oils. These definitions for fats and oils are described in Streitwieser and Heathcock, *Introduction to Organic Chemistry* pp. 506-509 (1976), this publication incorporated herein by reference.

The term "substantially free from anioinc surfactants" means that the compositisions of the instant invention contain less than about 1% of an anionic surfactant, and preferably do not contain any anionic surfactant.

Contact Angle

The contact angle is defined as the internal angle between a surface and a liquid droplet resting on that surface. High contact angles correspond to poor wetting of the surface by the liquid, while low contact angles signify good wetting. If a liquid spreads on the surface, the contact angle is considered to be zero and complete wetting is said to occur. Contact angle measurements can be employed to determine the wettability of human skin by a variety of liquids. These contact angles vary from 0° for highly lipophylic materials such as mineral oil to 108° for water and can be measured using a variety of techniques. See Rosenberg, A. et al. "Interaction Forces Involved in Wetting of Human Skin," *Journal of Pharmaceutical Sciences.* vol. 62, no. 6, pp. 920-921 (June 1973); Schott, H. "Contact Angles and Wettability of Human Skin", *Journal of Pharmaceutical Sciences.* vol. 60, no. 12, pp. 1893-1895 (December 1971); and Rosen, M. J. *Surfactants and Interfacial Phenomena,* second edition, pp.244-248 (1989); the disclosure of these publications being incorporated herein by reference.

The contact angle of sebum with skin, which has been treated with the compositions of the present invention, can be measured using various in vivo techniques. For example, a suitable site on the skin (such as the face, back of the hand, forearm, etc.) can be cleansed and treated with the instant emulsion composition (about 2 mg/cm2), followed by application of a single drop of sebum (about 5-10µL). After about one minute, the contact angle of the sebum with the skin can be directly determined using a macroscope at 25× magnification (Scopeman ® MS503, available from Moritex USA, Inc., San Diego, Calif.), or alternatively can be determined from a video image or photograph. Preferred contact angles for sebum with skin treated with the emulsions of the instant invention are preferably between 0° and about 15°, more preferably between 0° and about 12°, and most preferably between 0° and about 10°.

Sebum Migration

Sebum migration and the effects of skin care products on this migration can be measured by various in vivo techniques. For example, a suitable site on the skin (such as the face, back of the hand, forearm, etc.) can be cleansed and treated with the instant emulsion composition (about 2 mg/cm$^2$), followed by application of a single drop of sebum (about 1-10 µL). The spreading of the sebum can be determined by directly measuring the surface area of the sebum as a function of time or from video images or photographs of the sebum recorded at appropriate time intervals. The areas can be measured either in absolute units (e.g. cm$^2$, mm$^2$) or in other relative units (e.g. the number of pixels on a video cathode ray tube). A pixel is a single element which contstitutes an image on a video cathode ray tube screen.

For example, for determining sebum migration rates it is found particularly convenient to measure the rate as the change in area in pixels per unit time in minutes. The rate of sebum migration is most conveniently reported in pixels per 5 minute time interval.

The preferred rate of sebum migration for the emulsions of the instant invetion is greater than about 8300 pixels over the period from 0 to 5 minutes. A more preferred rate is greater than about 8500 pixels over the period from 0 to 5 minutes. An even more preferred rate is greater than about 8700 pixels over the period from 0 to 5 minutes. An even further preferred rate is greater than about 9000 pixels over the period from 0 to 5 minutes. The most preferred rate is greater than about 9500 pixels over the period from 0 to 5 minutes.

Emulsions

The emulsion compositions of the present invention are of the oil-in-water type since these provide better aesthetic properties. The emulsions are readily prepared using art-recognized principles and methodologies in mixing the ingredients together and in choosing the type of mixing equipment to be used. Depending upon the choice of ingredients, the formulation has a semi-solid cream-like consistency which can be packaged in a plastic squeeze tube or glass jar or it has a lotion type consistency which can be packaged in a plastic squeeze container or bottle. The container can include a flow-type cap or pump-type dispenser.

The essential components of these emulsions include the following.

Essential Components

Cationic Surfactant

An essential component of the present compositions is a cationic surfactant which is present in the emulsion from about 0.01% to about 5%, more preferably from about 0.01% to about 2%, and most preferably from about 0.01% to about 1%. McCutcheon's, *Detergents and Emulsifiers*, North American Edition (1986), published by Allured Publishing Corporation, which is incorporated herein by reference, includes a broad listing of cationic surfactants.

Examples of cationic surfactants include distearyl dimethyl ammonium chloride, dilauryl dimethyl ammonium chloride, N-cetyl pyridinium bromide, alkyl dimethyl ethylbenzyl ammonium cyclohexyl sulfamate, dodecyl dimethyl ethylbenzyl ammonium chloride, alkyl triethanolammonium chloride, dimethyl di(hydrogenated tallow) ammonium chloride, Quaternium-15, bis(hydrogenated tallow alkyl)dimethyl methyl sulfates, y-gluconamidopropyldimethyl-2-hydroxyethyl ammonium chloride, decyl dimethyl octyl ammonium chloride, dimethyl 2-hydroxyethyl minkamidopropyl ammonium chloride, Quaternium-18 Methosulfate, isododecylbenzyl triethanolammonium chloride, cocamidopropyl dimethyl acetamido ammonium chloride, Quaternium-45, Quaternium-51, Quaternium-52, Quaternium-53, bis(N-hydroxyethyl-2-oleyl imidazolinium chloride) polyethylene glycol 600, lanolin/isosteramidopropyl ethyl dimethyl ammonium ethosulfate, bisamidopropyl-N,N-dimethyl-N-ethyl) ammonium methosulfate] dimer acid, Quaternium-62, Quaternium-63, stearamidopropyl dimethyl (myristyl acetate) ammonium chloride, and Quaternium-71. These hydrophobic cationic surfactants can be used either singly or as a combination of one or more materials.

The preferred hydrophobic cationic surfactants for use in this invention are the halide salts of N,N,N-trialkylaminoalkylene gluconamides having the formula:

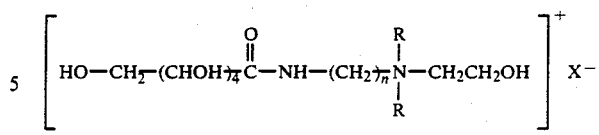

wherein R=alkyl, X=Cl⁻ or Br⁻, and n is an integer from 2 to 4.

Most preferred for use in this invention is y-gluconamidopropyl dimethyl 2-hydroxyethyl ammonium chloride (CTFA designation Quaternium-22) which has the following structure:

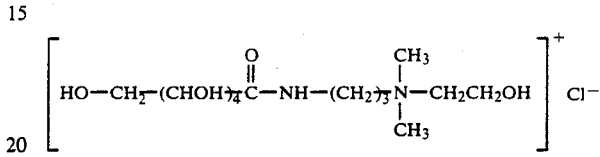

This compound is commercially available as a free-flowing, 60% aqueous solution from Van Dyk, Inc. (Belleville, N.J.) under the trademark Ceraphyl® 60. U.S. Pat. No. 3,855,290 to Zak et al., issued Dec. 17, 1974; U.S. Pat. No. 3,766,267 to Zak et al., issued Oct. 16, 1973; and U.S. Pat. No. 4,534,964 to Herstein et al., issued Aug. 13, 1985, which are all incorporated herein by reference, further describe Quaternium-22 and its use in personal care products.

Non-Volatile Organopolysiloxane

Another essential component is a non-volatile organopolysiloxane which is present from about 0.05% to about 10%, more preferably from about 0.1% to about 5%, and most preferably from about 0.1% to about 1%. The non-volatile silicone component is substantive to the skin and aids in redistributing sebum across the surface of the skin. Examples of such non-volatile silicones include dimethicone copolyol; dimethylpolysiloxane; diethylpolysiloxane; high molecular weight dimethicone (average molecular weight from about 200,000 to about 1,000,000 and, preferably, from about 300,000 to about 600,000) which can have various end-terminating groups such as hydroxyl, lower $C_1$-$C_3$ alkyl, lower $C_1$-$C_3$ alkoxy and the like; mixed $C_1$-$C_3$ alkyl polysiloxane (e.g., methylethylpolysiloxane); phenyl dimethicone and other aryl dimethicones; and dimethiconol; and mixtures thereof. Preferred is dimethiconol which is a dimethyl silicone polymer terminated with hydroxyl groups. Dimethiconol is available as Q2-1401 Fluid, a solution of 13 percent ultra-high-viscosity dimethiconol in volatile cyclomethicone fluid as a carrier, and Q2-1403 Fluid, a solution of ultra-high-viscosity dimethiconol fluid in dimethicone (both sold by Dow Corning Corporation).

Carboxylic Acid Copolymer

Another essential component of the compositions of the present invention is a carboxylic acid copolymer. These copolymers consist essentially of a colloidally water-soluble polymer of acrylic acid crosslinked with a polyalkenyl polyether of a polyhydric alcohol, and optionally an acrylate ester or a polyfunctional vinylidene monomer.

Preferred copolymers useful in the present invention are polymers of a monomeric mixture containing 95.9 to 98.8 weight percent of an olefinically unsaturated carboxylic monomer selected from the group consisting of acrylic, methacrylic and ethacrylic acids; about 1 to about 3.5 weight percent of an acrylate ester of the formula:

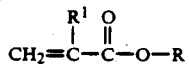

wherein R is an alkyl radical containing 10 to 30 carbon atoms and $R^1$ is hydrogen, methyl or ethyl; and 0.1 to 0.6 weight percent of a polymerizable cross-linking polyalkenyl polyether of a polyhydric alcohol containing more than one alkenyl ether group per molecule wherein the parent polyhydric alcohol contains at least 3 carbon atoms and at least 3 hydroxyl groups.

Preferably, these polymers contain from about 96 to about 97.9 weight percent of acrylic acid and from about 2.5 to about 3.5 weight percent of acrylic esters wherein the alkyl group contains 12 to 22 carbon atoms, and $R^1$ is methyl, most preferably the acrylate ester is stearyl methacrylate. Preferably, the amount of cross-linking polyalkenyl polyether monomer is from about 0.2 to 0.4 weight percent. The preferred crosslinking polyalkenyl polyether monomers are allyl pentaerythritol, trimethylolpropane diallylether or allyl sucrose. These polymers are fully described in U.S. Pat. No. 4,509,949, to Huang et al., issued Apr. 5, 1985, this patent being incorporated herein by reference.

Other preferred copolymers useful in the present invention are the polymers which contain at least two monomeric ingredients, one being a monomeric olefinically-unsaturated carboxylic acid, and the other being a polyalkenyl, polyether of a polyhydric alcohol. Additional monomeric materials may be present in the monomeric mixture if desired, even in predominant proportion.

The first monomeric ingredient useful in the production of these carboxylic polymers are the olefinically-unsaturated carboxylic acids containing at least one activated carbon-to-carbon olefinic double bond, and at least one carboxyl group. The preferred carboxylic monomers are the acrylic acids having the general structure

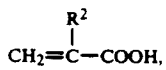

wherein $R^2$ is a substituent selected from the class consisting of hydrogen, halogen, and the cyanogen (—C≡N) groups, monovalent alkyl radicals, monovalent alkaryl radicals and monovalent cycloaliphatic radicals. Of this class, acrylic, methacrylic, and ethacrylic acid are most preferred. Another useful carboxylic monomer is maleic anhydride or the acid. The amount of acid used will be from about 95.5 to about 98.9 weight percent of the total monomers used. More preferably the range will be from about 96 to about 97.9 weight percent.

The second monomeric ingredient useful in the production of these carboxylic polymers are the polyalkenyl polyethers having more than one alkenyl ether grouping per molecule. The most useful possess alkenyl groups in which an olefinic double bond is present attached to a terminal methylene grouping, $CH_2=C<$.

The additional monomeric materials which may be present in the polymers include polyfunctional vinylidene monomers containing at least two terminal $CH_2<$ groups, including for example, butadiene, isoprene, divinyl benzene, divinyl naphthalene, allyl acrylates, and the like. These polymers are fully described in U.S. Pat. No. 2,798,053, to Brown, H. P., issued July 2, 1957, this patent being incorporated herein by reference.

Examples of carboxylic acid copolymers useful in the present invention include Carbomer 934, Carbomer 941, Carbomer 950, Carbomer 951, Carbomer 954, Carbomer 980, Carbomer 981, Carbomer 1342, and Acrylates/$C_{10-30}$ Alkyl Acrylate Cross Polymers (available as Carbopol 934, Carbopol 941, Carbopoly 950, Carbopol 951, Carbopol 954, Carbopol 980, Carbopol 981, Carbopol 1342, and the Pemulen Series, respectively, from B. F. Goodrich).

Other carboxylic acid copolymers useful in the present invention include sodium salts of acrylic acid/acrylamide copolymers sold by the Hoechst Celanese Corporation under the trademark of Hostaceren PN73. Also included are the hydrogel polymers sold by lipo Chemicals Inc. under the trademark of HYPAN hydrogels. These hydrogels consist of crystalline plicks of nitrites on a C—C backbone with various other pendant groups such as carboxyls, amides, and amidines. An example would include HYPAN SA100 H, a polymer powder available from Lipo Chemical.

Neutralizing agents suitable for use in neutralizing acidic group containing copolymers herein include sodium hydroxide, potassium hydroxide, ammonium hydroxide, monoethanolamine, diethanolamine, triethanolamine, tetrahydroxypropyl ethylenediame (available as the Quadrol® series from BASF), tris, arginine, triisopropylamine and lysine.

The carboxylic acid copolymers can be used individually or as a mixture of two or more polymers and comprise from about 0.025% to about 0.75%, preferably from about 0.05% to about 0.25%, and most preferably from about 0.075% to about 0.175% of the compositions of the present invention.

For the present invention the weight ratio of carboxylic acid copolymer to cationic surfactant is preferably from about 1:10 to about 10:1.

Humectant The last essential component of the compositions of the present invention is a humectant. A variety of humectants can be employed in the compositions of the present invention and can be present at a level of from about 1% to about 10%, more preferably from about 2% to about 8% and most preferably from about 3% to about 5%. These humectants include urea; guanidine; glycolic acid and glycolate salts (e.g. ammonium and quaternary alkyl ammonium); lactic acid and lactate salts (e.g. ammonium and quaternary alkyl ammonium); polyhydroxy alcohols such as sorbitol, glycerin, hexanetriol, propylene glycol, hexylene glycol and the like; polyethylene glycol; sugars and starches; sugar and starch derivatives (e.g. alkoxylated glucose); D-panthenol; hyaluronic acid; lactamide monoethanolamine; acetamide monoethanolamine; and mixtures thereof.

Preferred humectants for used in the compositions of the present invention are the $C_3-C_6$ diols and triols. Especially preferred is the triol, glycerin.

Optional Components

Each of the water and oil phases of the oil-in-water emulsion may contain optional components, which can comprise a wide variety of cosmetic and pharmacologic additives. Typical of such optional components are:

Sunscreens A wide variety of one or more conventional sunscreening agents are suitable for use in the present invention. Segarin, et al., at Chapter VIII, pages 189 et seq., of *Cosmetics Science and Technology*, disclose numerous suitable agents. Specific suitable sunscreening agents include, for example: ethylhexyl-p-methoxycinnamate (available as Parsol MCX from Givaudan Corporation), p-Aminobenzoic acid, its salts and its derivatives (ethyl, isobutyl, glyceryl esters; p-dimethylaminobenzoic acid; 2-ethylhexyl N,N-dimethylaminobenzoate); Anthranilates (i.e., o-aminobenzoates; methyl, octyl, amyl, menthyl, phenyl, benzyl, phenylethyl, linalyl, terpinyl, and cyclohexenyl esters); Salicylates (octyl, amyl, phenyl, benzyl, menthyl, glyceryl, and dipropyleneglycol esters); Cinnamic acid derivatives (menthyl and benzyl esters, -phenyl cinnamonitrile; butyl cinnamoyl pyruvate); Dihydroxycinnamic acid derivatives (umbelliferone, methylumbelliferone, methylaceto-umbelliferone); Trihydroxycinnamic acid derivatives (esculetin, methylesculetin, daphnetin, and the glucosides, esculin and daphnin); Hydrocarbons (diphenylbutadiene, stilbene); Dibenzalacetone and benzalacetophenone; Naphtholsulfonates (sodium salts of 2-naphthol 3,6-disulfonic and of 2-naphthol-6,8-disulfonic acids); Dihydroxy-naphthoic acid and its salts; o- and p-Hydroxybiphenyldisulfonates; Coumarin derivatives (7-hydroxy, 7-methyl, 3-phenyl); Diazoles (2-acetyl-3-bromoindazole, phenyl benzoxazole, methyl naphthoxazole, various aryl benzothiazoles); Quinine salts (bisulfate, sulfate, chloride, oleate, and tannate); Quinoline derivatives (8-hydroxyquinoline salts, 2-phenylquinoline); Hydroxymethoxy-substituted benzophenones; Uric and vilouric acids; Tannic acid and its derivatives (e.g., hexaethylether); (Butyl carbityl) (6-propyl piperonyl) ether; Hydroquinone; Benzophenones (Oxybenzene, Sulisobenzone, Dioxybenzone, Benzoresorcinol, 2,2′,4,4′-Tetrahydroxybenzophenone 2,2′-Dihydroxy-4,4′-dimethoxybenzophenone, Octabenzone; 4-Isopropyldibenzoylmethane; Butylmethoxydibenzoylmethane; Octocrylene; 4-isopropyl-di-benzoylmethane; and camphor derivatives such as methyl benzylidene or benzylidene camphor; and mixtures thereof. Other sunscreens include the solid physical sunblocks such as titanium dioxide (micronized titanium dioxide, 0.03 microns), zinc oxide, silica, iron oxide and the like. Without being limited by theory, it is believed that these inorganic materials provide a sunscreening benefit through reflecting, scattering, and absorbing harmful UV, visible, and infrared radiation.

A safe and photoprotectively effective amount of sunscreen may be used in the sunscreen compositions of the present invention. By "safe and photoprotectively" is meant an amount sufficient to provide photoprotection when the composition is applied, but not so much as to cause any side effects or skin reactions. Generally, the sunscreen agent may comprise from about 0.5% to about 20% of the composition. An additional sunscreen agent may comprise from about 0.5% to about 30%, preferably from about 0.5% to about 20%, of the composition. Exact amounts will vary depending upon the sunscreen chosen and the desired Sun Protection Factor (SPF). Particularly useful is the sunscreen ethylhexyl-p-methoxycinnamate either alone or in combination with the physical sunscreen titanium dioxide.

SPF is a commonly used measure of photoprotection of a sunscreen against erythema. This number is derived from another parameter, the minimal erythemal dose (MED). MED is defined as the "lease exposure dose at a specified wavelength that will elicit a delayed erythema response". The MED indicates the amount of energy reaching the skin and the responsiveness of the skin to the radiation. The SPF of a particular photoprotector is obtained by dividing the MED of protected skin by the MED of unprotected skin. The higher the SPF, the more effective the agent in preventing sunburn. The SPF value tells how many times longer a person can stay in the sun with use of the sunscreen (compared to the same person with unprotected skin) before that person will experience 1 MED. For example, utilizing a sunscreen with an SPF of 6 will allow an individual to stay in the sun six times longer before receiving MED. As the SPF value of a sunscreen increases, the less chance exists for development of tanning of the skin. Commercially available sunscreening products have SPF values ranging from 2 to 50.

Also particularly useful either alone or along with ethylhexyl-p-methoxycinnamate are sunscreens such as those disclosed in U.S. Pat. No. 4,937,370, to Sabatelli, issued June 26, 1990; and Sabatelli et al., U.S. patent application Ser. No. 054,046 (filed June 2, 1987). The sunscreening agents disclosed therein have, in a single molecule, two distinct chromophore moieties which exhibit different ultra-violet radiation absorption spectra. One of the chromophore moieties absorbs predominantly in the UVB radiation range and the other absorbs strongly in the UVA radiation range.

These sunscreening agents provide higher efficacy, broader UV absorption, lower skin penetration and longer lasting efficacy relative to conventional sunscreens.

Preferred members of this class of sunscreening agents are 4-N,N-(2-ethylhexyl)methylaminobenzoic acid ester of 2,4-dihydroxybenzophenone; N,N-di-(2-ethylhexyl)-4-aminobenzoic acid ester with 4-hydroxydibenzoylmethane; 4-N,N-(2-ethylhexyl) methylaminobenzoic acid ester with 4-hydroxydibenzoylmethane; 4-N,N-(2-ethylhexyl)methylaminobenzoic acid ester of 2-hydroxy-4-(2-hydroxyethoxy)benzophenone; 4-N,N-(2-ethylhexyl) methylaminobenzoic acid ester of 4-(2-hydroxyethoxy)dibenzoylmethane; N-N-di-(2-ethylhexyl)-4-aminobenzoic acid ester of 2-hydroxy-4-(2-hydroxyethoxy)benzophenone, and N,N-di-(2-ethylhexyl)4-aminobenzoic acid ester of 4-(2-hydroxyethoxy)dibenzoylmethane and mixtures thereof.

Volatile Silicone Fluids

Volatile silicone oils useful in the compositions of the present invention are preferably cyclic. The following formula illustrates cyclic volatile polydimethylsiloxanes useful in the compositions disclosed herein:

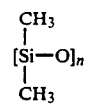

wherein n equals about 3 to about 7. Linear polydimethylsiloxanes contain from about 3 to about 9 silicon atoms per molecule and have the following general formula:

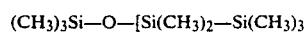

wherein n equals about 1 to about 7. Linear volatile silicone materials generally have viscosities of less than about 5 centistokes at 25° C. while cyclic materials typically have viscosities of less than about 10 centistokes. A description of various volatile silicone oils is found in Todd, et al., "Volatile Silicone Fluids for Cosmetics", *Cosmetics & Toiletries*, 91. pages 27-32 (1976), the disclosures of which are incorporated by reference herein in their entirety.

Examples of preferred volatile silicone oils useful herein include: Dow Corning 344, Dow Corning 345, and Dow Corning 200 (manufactured by Dow Corning Corp.); Silicone 7207 and Silicone 7158 (manufactured by the Union Carbide Corp.); SF 1202 (manufactured by General Electric); and SWS-03314 (manufactured by SWS Silicones, Inc.). Cyclomethicone, dimethicone, decamethylcyclohexasioxane, hexamethyldisioloxane, simethicone, and mixtures thereof.

Emollients

The compositions of the present invention preferably comprise at least one emollient. Preferred emollients are volatile silicone oils, non-volatile emollients, and the highly branched hydrocarbons known as the Permethyl 99 through 108A series (available from Permethyl Corporation) and mixtures thereof. The compositions of the present invention more preferably comprise at least one volatile silicone oil which functions as a liquid emollient, or especially in a mixture of volatile silicone oils and non-volatile emollients. The term "volatile", as used herein, refers to those materials which have a measurable vapor pressure at ambient temperature.

The present compositions also preferably contain one or more non-volatile emollients. Such materials include fatty acid and fatty alcohol esters hydrocarbons and mixtures thereof. Emollients among those useful herein are described in 1 *Cosmetics, Science and Technology* 27-104 (M. Balsam and E. Sagarin, Ed.; 1972), and U.S. Pat. No. 4,202,879, to Shelton, issued May 13, 1980 (both incorporated by reference herein).

Non-polar fatty acid and fatty alcohol esters useful herein as an emollient material include, for example, di-isopropyl adipate, isopropyl myristate, isopropyl palmitate, ethyl hexyl palmitate, isodecyl neopentanoate $C_{12}-C_{15}$ alcohol benzoate, diethyl hexyl maleate, PPG 14 butyl ether and PPG-2 myristyl ether propionate. Hydrocarbons such as isohexadecane (e.g., Permethyl 101A supplied by Presperse) are also useful as emollients.

The emollients typically comprise in total from about 1% to about 50%, preferably from about 1% to about 25%, and more preferably from about 1% to about 10% by weight of the compositions of the present invention.

Waxes

An optional component of the compositions herein is a wax. Useful ester waxes include $C_{10}-C_{40}$ alcohols esterfied with $C_{10}-C_{40}$ fatty acid, diesters of $C_{10}-C_{40}$ fatty acid where the alcohol is propylene glycol, ethylene glycol, polyethylene glycol, polypropylene glycol, polyglycerin, pentaerythritol tri- or tetra- esters of $C_{10}-C_{40}$ fatty acids, $C_{10}-C_{40}$ fatty acids of sorbitan triesters, $C_{10}-C_{40}$ fatty acids of sucrose polyesters having 3-8 moles of substitution, myristyl myristate, paraffin, synthetic waxes such as Fischer-Tropsche waxes, microcrystalline waxes, castor wax, behenyl behenrate and myristyl propionate and mixtures thereof. Useful diester waxes include Synchrowax ERL-C (available from Croda) and propylene glycol diester waxes including ethylene glycol distearate and glycol distearate.

Pharmaceutical Actives

Pharmaceutical actives useful in the present invention include any chemical material or compound suitable for topical administration which induces any desired local or systemic effect. Such substances include, but are not limited to antibiotics, antiviral agents, analgesics (e.g. ibuprofen, acetyl salicylic acid, naproxen, and the like), antihistamines, antiinflammatory agents, antipruritics, antipyretics, anesthetic agents, diagnostic agents, hormones, antifungals, antimicrobials, cutaneous growth enhancers, pigment modulators, antiproliferatives, antipsoriatics, retinoids, anti-acne medicaments (e.g. benzoyl peroxide, sulfur, etc.), antineoplastics agents, phototherapeutic agents, and keratolytics (e.g. resorcinol, salicylic acid), and mixtures thereof. These pharmaceutical actives can be incorporated in the emulsions preferably from about 0.1% to about 20%.

Vitamins

Various vitamins may also be included in the compositions of the present invention. For example, Vitamin A, and derivatives thereof, ascorbic acid, Vitamin B, biotin, panthothenic acid, Vitamin D, and mixtures thereof may be used. Vitamin E, tocopherol acetate and derivatives may also be used.

Other Optional Components

A variety of additional ingredients may be added to the emulsion compositions of the present invention. These additional ingredients include various polymers for aiding the film-forming properties and substantivity of the formulation, preservatives for maintaining the antimicrobial integrity of the compositions, antioxidants, and agents suitable for aesthetic purposes such as fragrances, pigments, and colorings.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention.

EXAMPLE I

A leave-on facial emulsion composition containing a cationic hydrophobic surfactant is prepared by combining the following components utilizing conventional mixing techniques.

| Ingredient | % Weight |
| --- | --- |
| Water | qs |
| Glycerin | 3.00 |
| Cetyl Palmitate | 3.00 |
| Cetyl Alcohol | 1.26 |
| Quaternium-22 | 1.00 |
| Glyceryl Monohydroxy Stearate | 0.74 |
| Dimethicone | 0.60 |
| Stearic Acid | 0.55 |
| Octyldodecyl Myristate | 0.30 |
| Potassium Hydroxide | 0.20 |
| Carbomer 1342 | 0.125 |
| Tetrasodium EDTA | 0.10 |
| DMDM Hydantoin and Iodopropynyl Butyl Carbamate | 0.10 |

| Ingredient | % Weight |
|---|---|
| Carbomer 951 | 0.075 |

This emulsion is useful for providing control of the distribution of sebum on the skin.

Use of an amount of this composition sufficient to deposit about 2.0 mg/cm² on the skin ould give a contact angle of 10° between sebum and skin.

The rate of sebum migration for the emulsion would be greater than 9500 pixels over the period from 0-5 minutes.

EXAMPLE II

A leave-on facial emulsion composition containing both a cationic hydrophobic surfactant and a non-volatile organopolysiloxane is prepared by combining the following components utilizing conventional mixing techniques.

| Ingredient | % Weight |
|---|---|
| Water | qs |
| Glycerin | 3.00 |
| Cetyl Palmitate | 3.00 |
| Cetyl Alcohol | 1.26 |
| Quaternium-22 | 1.00 |
| Glyceryl Monohydroxy Stearate | 0.74 |
| Dimethicone | 0.60 |
| Stearic Acid | 0.55 |
| Cyclomethicone and Dimethiconol | 0.50 |
| Octyldodecyl Myristate | 0.30 |
| Potassium Hydroxide | 0.20 |
| Carbomer 1342 | 0.125 |
| Tetrasodium EDTA | 0.10 |
| DMDM Hydantoin and Iodopropynyl Butyl Carbamate | 0.10 |
| Carbomer 951 | 0.075 |

This emulsion is useful for providing control of the distribution of sebum on the skin.

Use of an amount of this composition sufficient to deposit about 2.0 mg/cm² on the skin would give a contact angle of 10° between sebum and skin.

The rate of sebum migration for the emulsion would be greater than 9500 pixels over the period from 0-5 minutes.

What is claimed is:

1. A leave-on facial emulsion composition, substantially free from fats and oils and anionic surfactants, comprising:
   (a) from about 0.01 to about 5% of a cationic surfactant;
   (b) from about 0.1 to about 10% of a non-volatile organopolysiloxane having an average molecular weight of at least 200,000;
   (c) from about 0.01 to about 5% of one or more of a carboxylic acid copolymer;
   (d) from about 1% to about 10% of a humectant; and
   (e) a cosmetically acceptable carrier; wherein said composition provides a contact angle between sebum and skin from 0° to about 10°, and a spreading index for sebum migration greater than about 8300 pixels over the time period from 0-5 minutes.

2. An emulsion as in claim 1 wherein the cationic surfactant is an N,N,N-trialkylaminoalkylene gluconamide of the formula

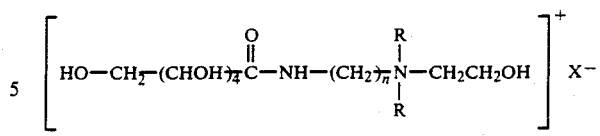

wherein R = alkyl, X = Cl— or Br—, and n is an integer from 2 to 4.

3. An emulsion as in claim 2 wherein the cationic surfactant is γ-gluconamidopropyl dimethyl 2-hydroxyethyl ammonium chloride.

4. An emulsion as in claim 3 wherein the non-volatile organopolysiloxane is selected from the group consisting of dimethicone copolyol, dimethylpolysiloxane, diethylpolysiloxane, high molecular weight dimethicone, mixed $C_1$-$C_3$ alkyl polysiloxane, phenyl dimethicone, dimethiconol, and mixtures thereof.

5. An emulsion as in claim 4 wherein the non-volatile organopolysiloxane is dimethiconol.

6. An emulsion as in claim 5 wherein the humectant is a $C_3$-$C_6$ diol or triol.

7. An emulsion as in claim 6 wherein the humectant is glycerin.

8. An emulsion as in claim 7 wherein the weight ratio of carboxylic acid copolymer to gluconamide is from about 1:10 to about 10:1.

9. An emulsion as in claim 8 wherein the carboxylic acid copolymer is selected from the group consisting of Carbomer 941, Carbomer 951, Carbomer 981, Carbomer 1342, and mixtures thereof.

10. An emulsion as in claim 1 wherein said emulsion further comprises from about 0.1% to about 20% of a pharmaceutical active.

11. An emulsion as in claim 1 wherein said emulsion further comprises from about 0.5% to about 20% of a sunscreening agent.

12. An emulsion as in claim 11 wherein said sunscreening agent is selected from the group consisting of ethylhexyl-p-methoxycinnamate, octocrylene, and 2-ethylhexyl N,N-dimethylaminobenzoate.

13. An emulsion as in claim 12 wherein said sunscreening agent is ethylhexyl-p-methoxycinnamate.

14. An emulsion as in claim 13 wherein said emulsion further comprises from about 0.5% to about 30% titanium dioxide.

15. A method for controlling sebum distribution on facial skin, said method comprising topically applying to the facial skin an effective amount of an emulsion composition according to claim 1.

16. A method for controlling sebum distribution on facial skin, said method comprising topically applying to the facial skin an effective amount of an emulsion composition according to claim 2.

17. A method for controlling sebum distribution on facial skin, said method comprising topically applying to the facial skin an effective amount of an emulsion composition according to claim 3.

18. A method for controlling sebum distribution on facial skin, said method comprising topically applying to the facial skin an effective amount of an emulsion composition according to claim 5.

19. A method for controlling sebum distribution on facial skin, said method comprising topically applying to the facial skin an effective amount of an emulsion composition according to claim 7.

20. A method for controlling sebum distribution on facial skin, said method comprising topically applying to the facial skin an effective amount of an emulsion composition according to claim 14.

* * * * *